(12) United States Patent
Fujii

(10) Patent No.: US 8,825,448 B2
(45) Date of Patent: Sep. 2, 2014

(54) SPECTROSCOPIC REFLECTOMETER

(75) Inventor: Fumitaka Fujii, Kyoto (JP)

(73) Assignee: Horiba, Ltd. (JP)

( * ) Notice: Subject to any disclaimer, the term of this patent is extended or adjusted under 35 U.S.C. 154(b) by 391 days.

(21) Appl. No.: 12/852,734

(22) Filed: Aug. 9, 2010

(65) Prior Publication Data

US 2011/0035189 A1 Feb. 10, 2011

(30) Foreign Application Priority Data

Aug. 7, 2009 (JP) ................................ 2009-185007

(51) Int. Cl.
*G01N 21/27* (2006.01)
*G01N 21/55* (2014.01)

(52) U.S. Cl.
CPC .............. *G01N 21/274* (2013.01); *G01N 21/55* (2013.01)
USPC .......................................... 702/189; 356/448

(58) Field of Classification Search
CPC .............................. G01N 21/274; G01N 21/55
USPC .......................................... 702/189; 356/488
See application file for complete search history.

(56) References Cited

U.S. PATENT DOCUMENTS

| | | | | |
|---|---|---|---|---|
| 4,566,798 | A * | 1/1986 | Haas | 356/448 |
| 7,126,131 | B2 * | 10/2006 | Harrison | 250/372 |
| 2003/0090655 | A1 * | 5/2003 | Norton et al. | 356/326 |
| 2003/0231319 | A1 | 12/2003 | Zhang et al. | |
| 2005/0206907 | A1 | 9/2005 | Fujimoto et al. | |
| 2007/0181795 | A1 * | 8/2007 | Walsh et al. | 250/252.1 |

FOREIGN PATENT DOCUMENTS

| | | |
|---|---|---|
| CN | 1293361 A | 5/2001 |
| CN | 1379225 A | 11/2002 |
| CN | 1556914 A | 12/2004 |
| JP | 2005-3401 A | 1/2005 |
| JP | 2005-265655 A | 9/2005 |
| JP | 2008-20332 A | 1/2008 |
| JP | 2009-53157 A | 3/2009 |
| WO | 03025497 A1 | 3/2003 |
| WO | 2010/013429 A1 | 2/2010 |

OTHER PUBLICATIONS

RCA, "Photomultiplier Manual", Sep. 1970, RCA; http://archive.org/details/RcaPhotomultiplierManual note select "pdf with text".*

(Continued)

*Primary Examiner* — Jonathan C Teixeira Moffat
*Assistant Examiner* — Regis Betsch
(74) *Attorney, Agent, or Firm* — Cantor Colburn LLP

(57) ABSTRACT

In a spectroscopic reflectometer, in order to make it possible to omit a supplementary measurement (specifically, measurement of a calibration sample) which has been needed every time a light reflectance of an inspection work is measured to promote the reduction in measurement time and simplification in measurement configuration, an internal reflection mechanism having a constant light reflectance is arranged inside a head so that light reflected by the internal reflection mechanism is received by a photo-detector, whereby the light reflectance of the inspection work is calculated based on an output value of the photo-detector in a state of having substantially no light introduced, an output value of the photo-detector when a dark sample that substantially reflects no light is used, an output value that is an output value of the photo-detector when a calibration sample of a known light reflectance is used as the object, and an output value of the photo-detector when an inspection work to be measured is used.

6 Claims, 13 Drawing Sheets

(56) References Cited

OTHER PUBLICATIONS

Decision to Grant a Patent issued in Japanese patent application No. 2009-185007, dated Jun. 18, 2103 (English translation not available).

Chinese Office Action for CN Patent Application 20100250005.1 dated Nov. 20, 2013 with partial English translation.

* cited by examiner

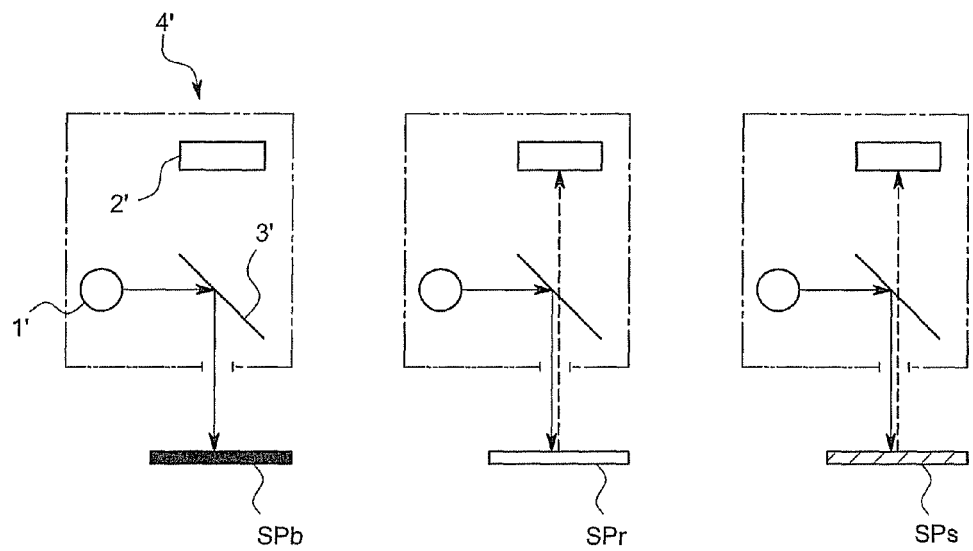
FIG. 1(a)
MEASUREMENT OF DARK SAMPLE
FIG. 1(b)
MEASUREMENT OF CALIBRATION SAMPLE
FIG. 1(c)
MEASUREMENT OF INSPECTION WORK
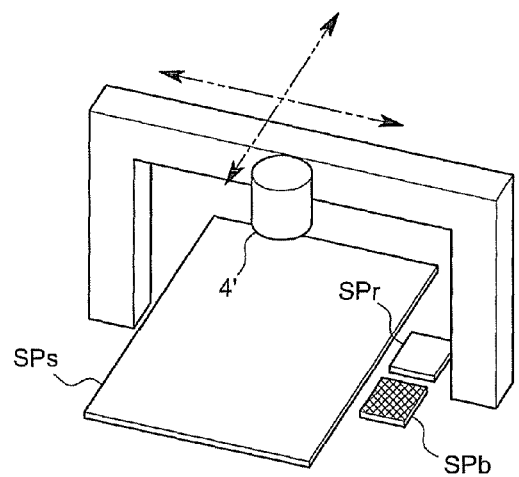
FIG. 2

FIRST EMBODIMENT: SUBORDINATE MEASUREMENT (MEASUREMENT OF DARK SAMPLE)

$$I_b = \alpha I_0 + I_d$$

FIRST EMBODIMENT: SUBORDINATE MEASUREMENT (MEASUREMENT OF CALIBRATION SAMPLE)

$$I_r = \beta R_r I_0 + \alpha I_0 + I_d$$

FIRST EMBODIMENT: MAIN MEASUREMENT (MEASUREMENT OF DARK SAMPLE)

$$I_b' = \alpha I_0' + I_d'$$

FIRST EMBODIMENT: MAIN MEASUREMENT (MEASUREMENT OF INSPECTION WORK)

$$I_s' = \beta R_s I_0' + \alpha I_0' + I_d'$$

SPECTROSCOPIC REFLECTOMETER

TECHNICAL FIELD

The present invention generally relates to a spectroscopic reflectometer, and in particular to a reflectance measurement mechanism for measuring a light reflectance of an inspection work to be measured.

BACKGROUND ART

The spectroscopic reflectometer is a measuring instrument, which irradiates measurement light to an inspection work such as a film body to be measured and generates a spectrum of interference light of reflection light reflected by a surface thereof and transmitted reflection light which transmits the inside of the inspection work and reflected by an opposite boundary face and gets out of the surface, whereby a film thickness of the inspection work is obtained based on the spectrum for measurement, as shown in Patent Document 1.

In such a spectroscopic reflectometer, it is necessary to measure an optical reflectance of the inspection work. Therefore, conventionally, as shown in FIGS. 1(a), 1(b) and 1(c), light is irradiated from a light source 1' respectively to a calibration sample $SP_r$ having a known and constant reflectance and is also applied to a dark sample $SP_b$ which does not have any reflection light at all, and an output value of a photo-detector 2' is measured in each of the cases. Then, an optical reflectance $R_s$ of the inspection work $SP_s$ is calculated from (Equation 1) as following. It is noted that, the reason of using the dark sample $SP_b$ for measurement is because the output value of the photo-detector 2' in a state of having no reflection light represents an offset value and this offset value should be cancelled.

$$R_s = \frac{I_s - I_b}{I_r - I_b} R_r \qquad \text{[Equation 1]}$$

Herein, Is is an output value of the photo-detector 2' with respect to the inspection work $SP_s$, $I_r$ is an output value of the photo-detector 2' with respect to the calibration sample $SP_r$, $I_b$ is an output value of the photo-detector 2' with respect to the dark sample $SP_b$, and $R_r$ is an optical reflectance (known) of the calibration sample $SP_r$.

Patent Document 1: JP2005-003401A

SUMMARY OF THE INVENTION

By the way, since there are actually recognized considerable variations in values of $I_r$ and $I_b$ in time base, conventionally the output values of the photo-detector 2' regarding the calibration sample $SP_r$ and the dark sample $SP_b$ are obtained every time the inspection work $SP_s$ is measured.

However, each sample must be replaced every measurement, and therefore there arises a problem that it takes expense in time and trouble to carry out the measurement. Particularly, in the case of measuring the calibration sample $SP_r$, the conditions such as a distance from a head 4' must be set almost the same as those of the inspection work $SP_s$, and the measurement thereof requires much expense in time and trouble.

So, for example, as shown in FIG. 2, there has been developed a device in which a head 4' is made movable so that a calibration sample $SP_r$ and a dark sample $SP_b$ placed in locations different from an inspection work $SP_s$ are to be measured by moving the head 4'. In this case, however, the configuration of the device becomes complicated and this may possibly raise a price to be high.

In consideration of such problems, the present invention has been made and an essential object thereof is to make it possible to omit a supplementary measurement (specifically, measurement of a calibration sample) which has been needed every time a light reflectance of an inspection work is measured, thereby promoting the reduction in measurement time and simplification in measurement configuration.

That is, a spectroscopic reflectometer according to one aspect of the present invention is characterized by including a head, a photo-detector, an internal reflection mechanism and a reflectance calculation unit as defined in the following features (1) to (4).

(1) The head is adapted to project measurement light to an object and introduce reflection light from the object irradiated by the measurement light.

(2) The photo-detector is adapted to detect an intensity of the received light, having its light receiving part placed in a position at which the reflection light introduced into the head arrives.

(3) The internal reflection mechanism has a constant light reflectance and is placed in a position at which a part of the measurement light arrives and the reflection light reflected by the internal reflection mechanism reaches the light receiving part of the photo-detector within the head.

(4) In a subordinate measurement period in which variation in the output value of the photo-detector is substantially negligible, the reflectance calculation unit measures, a first output value that is an output value of the photo-detector in a state of substantially no light being introduced, a second output value that is an output value of the photo-detector when a dark sample which substantially reflects no light is used as the object, and a third output value that is an output value of the photo-detector when a calibration sample of a known light reflectance is used as the object, and also, in a main measurement period in which variation in the output value of the photo-detector is substantially negligible, other than the subordinate measurement period, the reflectance calculation unit measures a fourth output value that is an output value of the photo-detector in a state of substantially no light being introduced, a fifth output value that is an output value of the photo-detector when the dark sample is used as the object, and a sixth output value that is an output value of the photo-detector when an inspection work to be measured is used as the object, whereby the light reflectance of the inspection work is calculated based on the first to sixth output values.

With the configuration as described above, it becomes possible to omit a measurement of a calibration sample which has been needed every time an inspection work is measured, thereby attaining the reduction in measurement time. Moreover, it becomes unnecessary to make a head movable to measure a calibration sample as conventionally adapted or to replace each of the samples, and therefore it becomes possible to promote simplification in configuration of the device and reduction in price.

This is because, to be summarized, the measurement value of the dark sample is not treated collectively as an offset amount as conventionally performed, but is strictly divided into factors that arise from the light source and factors that do not arise from the light source. That is, a specific feature of the present invention resides in the fact that the output value of the photo-detector in a state of substantially no light being introduced, i.e., the first output value is measured. Thus, only once the calibration sample is measured at a time of initial adjustment and the like, it becomes possible to measure the light reflectance of the inspection work by supplementing only the measurement of the dark sample at the time of measuring the inspection work after that. An example of this calculating method is described using Equations in an embodiment to be mentioned later.

In more specific, it is desirable that the reflectance calculation unit measures the first output value and the second output value in the main measurement period before or after the fourth output value is measured, i.e., a period in which variation in the output value of the photo-detector is negligible, and in the meanwhile, the reflectance calculation unit measures the third output value in a period other than the main measurement period and, differently from the measurement in the main measurement period, the reflectance calculation unit further measures the first output value and the second output value respectively in the subordinate measurement period before or after the third output value is measured in which variation in the output value of the photo-detector is negligible, whereby the light reflectance of the inspection work is calculated based on the fourth output value, first output value and second output value measured in the main measurement period and based on the third output value, first output value and second output value measured in the subordinate measurement period. It is noted here that "the variation in the output value of the photo-detector" means a total sum of variation in light quantity of the light source and variation due to a drift or offset of the detector per se.

Further, a spectroscopic reflectometer according to another aspect of the present invention is characterized by including a head, a photo-detector, an internal reflection mechanism and a reflectance calculation unit as defined in the following features (1) to (4).

(1) The head is adapted to project measurement light to an object and introduce reflection light from the object irradiated by the measurement light.

(2) The photo-detector is adapted to detect an intensity of the received light, having its light receiving part placed in a position at which the reflection light introduced into the head arrives.

(3) The internal reflection mechanism has a variable light reflectance in binary and is placed in a position at which a part of the measurement light arrives and the reflection light reflected by the internal reflection mechanism reaches the light receiving part of the photo-detector within the head.

(4) The reflectance calculation unit measures first to third output values to be described later by performing any one of following operations a and b in a subordinate period in which variation in the output value of the photo-detector is substantially negligible, and also measures, fourth to sixth output values to be described later by performing any one of following operations c and d in a main measurement period in which variation in the output value of the photo-detector is negligible, other than the subordinate measurement period, whereby the light reflectance of the inspection work is calculated based on the first to sixth output values.

(a.) The reflectance calculation unit measures the first and second output values that are output values of the photo-detector respectively when a dark sample which substantially reflects no light is used as the object and the light reflectance of the internal reflection mechanism is varied in binary, and measures the third output value that is an output value of the photo-detector when a calibration sample of a known light reflectance is used as the object and the light reflectance of the internal reflection mechanism is set to any one of the binary values.

(b.) The reflectance calculation unit measures the first output value that is an output value of the photo-detector when a dark sample which substantially reflects no light is used as the object and the light reflectance of the internal reflection mechanism is set to any one of the binary values, and measures the second and third output values that are output values of the photo-detector respectively when a calibration sample of a known light reflectance is used as the object and the light reflectance of the internal reflection mechanism is varied in binary.

(c.) The reflectance calculation unit measures the fourth and fifth output values that are output values of the photo-detector respectively when a dark sample which substantially reflects no light is used as the object and the light reflectance of the internal reflection mechanism is varied in binary, and measures the sixth output value that is an output value of the photo-detector when an inspection work to be measured is used as the object and the light reflectance of the internal reflection mechanism is set to any one of the binary values.

(d.) The reflectance calculation unit measures the fourth output value that is an output value of the photo-detector when a dark sample which substantially reflects no light is used as the object and the light reflectance of the internal reflection mechanism is set to any one of the binary values, and measures the fifth and sixth output values that are output values of the photo-detector respectively when an inspection work to be measured is used as the object and the light reflectance of the internal reflection mechanism is varied in binary.

Thus, the action and effect can be obtained similarly to the first aspect as described above. In specific, with this configuration, there can be also obtained an effect that it is unnecessary to provide an especial configuration for measuring an offset of the photo-detector per se.

In order to form an optical path for obtaining each of the output values with a simpler configuration, it is desirable to have a configuration such that, a beam splitter is arranged inside a main body of the head so that a part of the measurement light is reflected by the beam splitter to irradiate the object and a part of the measurement light is passed through the beam splitter to irradiate the internal reflection mechanism, and in the meanwhile, the reflection light reflected by the object is passed through the beam splitter to be guided to the photo-detector, and the reflection light reflected by the internal reflection mechanism is reflected to be guided to the photo-detector.

If the dark sample is incidental to the head movably and detachably between an irradiation position which is irradiated by the measurement light and an evacuation position which is not irradiated by the measurement light, since there is no need to move the head at the time of measuring the dark sample, a fixed type head can be implemented.

It is noted that the internal reflection mechanism is not limited to one exclusively provided in particular, and, for example, a configuration thereof may be provided using an inner wall of the head.

According to the present invention described above, it becomes possible to omit a measurement of a calibration sample which has been needed every time an inspection work is measured, thereby attaining reduction in measurement time. Moreover, since there is no need to make a head movable in order to measure a calibration sample as conventionally adapted or to replace each of the samples, it becomes possible to promote simplification in measurement configuration and reduction in price.

BRIEF DESCRIPTION OF DRAWINGS

FIGS. 1(a), 1(b) and 1(c) are schematic diagrams showing a measurement principle of a light reflectance in a conventional spectroscopic reflectometer;

FIG. 2 is a schematic perspective view showing a gist of the conventional spectroscopic reflectometer;

DESCRIPTION OF EMBODIMENTS

The following describes an embodiment of the present invention referring to the accompanying drawings.

First Embodiment

Dark Current Measurement System

Figure 3:
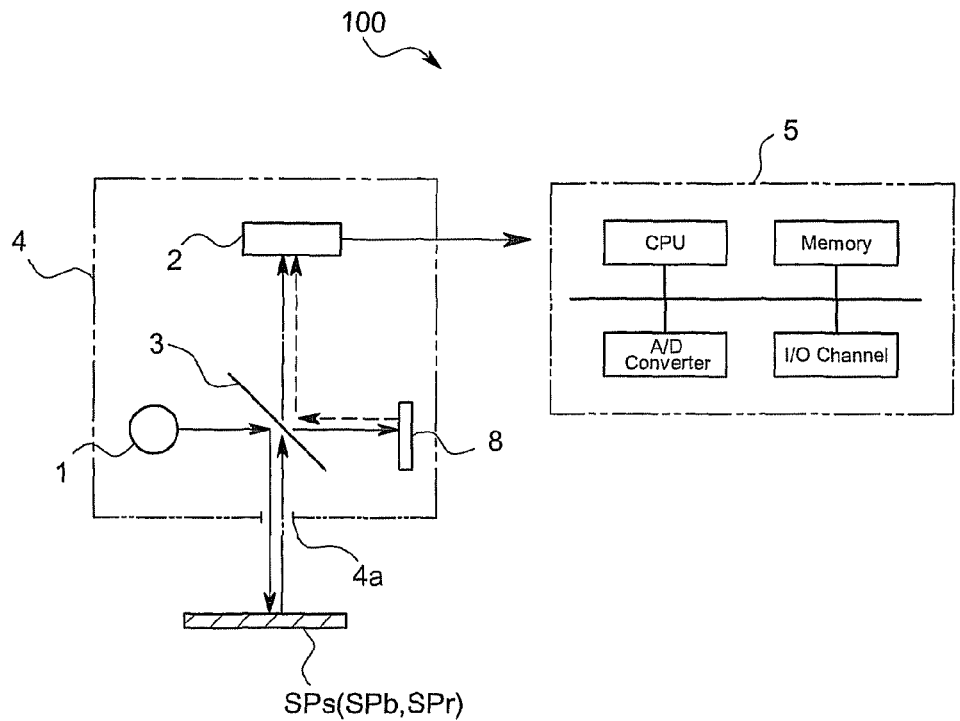
FIG. 3 is a schematic functional diagram of a spectroscopic reflectometer according to a first embodiment of the present invention.

A spectroscopic reflectometer 100 according to the present embodiment is suitably used for measurement of a thickness of a film for solar cells and a flat panel and is provided with a head 4, a photo-detector 2 and a reflectance calculation unit 5, as shown in FIG. 3. In the spectroscopic reflectometer 100, the head 4 projects measurement light toward an object such as an inspection work $SP_s$ and the like and introduces reflection light reflected by the object after irradiation with the measurement light, and the photo-detector 2 receives the reflection light introduced to the head 4 and detects the intensity thereof, whereby the reflectance calculation unit 5 calculates a light reflectance of the object based on an output values of the photo-detector 2.

In this embodiment, the measurement light is generated by a white light source 1 which is provided inside the head 4. However, the light source 1 may be separated from the head 4 so that the measurement light is guided to the head 4 via an optical fiber and the like.

Figure 4:
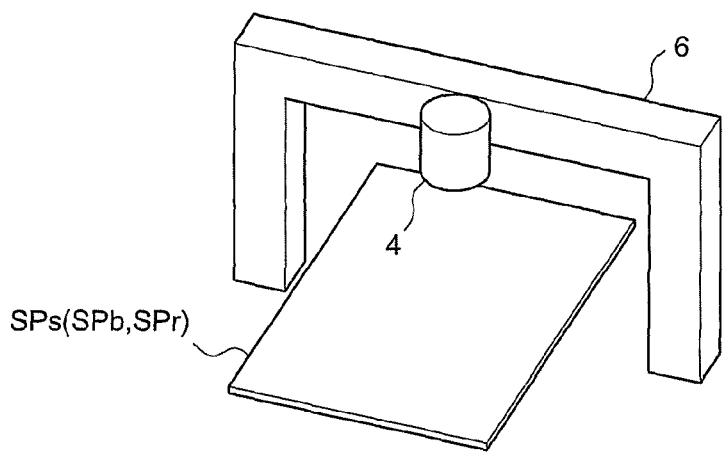
FIG. 4 is a schematic perspective view of the spectroscopic reflectometer according to the same embodiment.

As shown in FIGS. 3 and 4, the head 4 is formed of a hollow housing having a face opposing to, e.g., an inspection work $SP_s$ opened to be formed as a light inlet and outlet port 4a of the measurement light and the reflection light, and the head 4 is fixed and supported by, e.g., a support beam 6.

Figure 5:
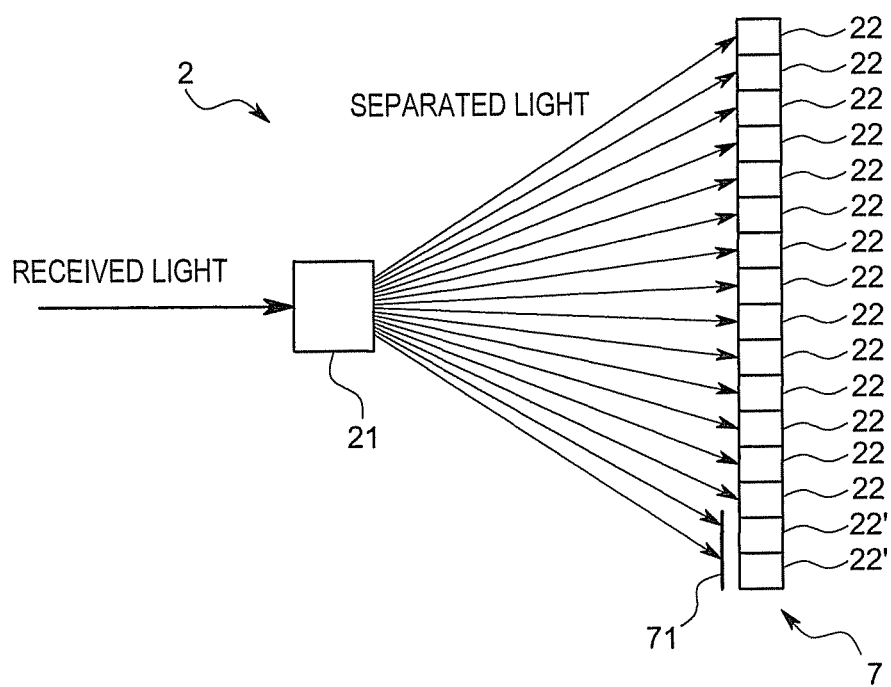
FIG. 5 is a schematic diagram of a photo-detector according to the same embodiment.

The photo-detector 2 has a spectral function and, for example, as shown in FIG. 5, the photo-detector 2 is provided with spectral means 21 adapted to spectroscope the received light every constant wavelength and sensor elements 22 such as CCDs, CMOS, photomultiplier and the like having an array of multiple channels that receive the lights respectively split every wavelength by the spectral means 21 and output electric signals of values each corresponding to the light intensity of each received light. In addition, an offset amount detection mechanism 7 is incidental to the photo-detector 2 so that the output value of the photo-detector 2 in a state of substantially receiving no light, i.e., an offset output value of each sensor element 22 can be detected. Specifically, this offset amount detection mechanism 7 includes a part of the sensor elements 22' and a mask member 71 for physically blocking the light to the part of the sensor elements 22'. Thus, the offset output values of the other sensor elements 22 can be calculated by estimation based on output values of the masked sensor elements 22'. As the estimation calculating method, there can be exemplified a method of making the offset output values of the sensor elements 22 identical to the offset output values of the masked sensor elements 22', and a method of previously measuring variations of the sensor elements 22 to the masked sensor elements 22' and calculating the offset output value of each of the sensor elements 22 based on the variations from the output values of the masked sensor elements 22'. Moreover, there can be considered a constitution such that, a shutter is previously provided in a light receiving portion of the photo-detector 2 and the output value of each of the sensor elements 22 when the light receiving portion is completely covered by the shutter so as not to enter the light is used as the offset output value.

In addition to the light source 1 and the photo-detector 2, a beam splitter 3 and an internal reflection mechanism 8 are arranged inside the head 4 as shown in FIG. 3. The beam splitter 3 is a translucent member of an iso-thickness flat plate shape having a characteristic of partly transmitting light and partly reflecting the light. In this embodiment, the beam splitter 3 is arranged in a manner such that, the surface of the beam splitter 3 is inclined at an angle of 45° with respect to an optical axis of the measurement light projected from the light source 1, whereby a part of the measurement light reflected by the beam splitter 3 passes through the light inlet and outlet port 4a and is perpendicularly projected toward the surface of the object such as the inspection work $SP_s$. Further, the internal reflection mechanism 8 is arranged in a position facing the light source 1 across the beam splitter 3. This internal reflection mechanism 8 is an iso-thickness plate shaped member having a known and constant light reflectance, wherein the surface thereof is arranged to be perpendicular to the optical axis of the measurement light which has passed through the beam splitter 3 projected from the light source 1.

Therefore, the measurement light projected from the light source 1 is partly reflected by the beam splitter 3 and directed toward the object such as the inspection work $SP_s$. Then, the light is reflected by the object and the reflected light is directed to the beam splitter 3 again. Further, the light is partly passed through the beam splitter 3 and applied to the photo-detector 2. Meanwhile, the remaining part of the measurement light projected from the light source 1 and passed through the beam splitter 3 is reflected by the internal reflection mechanism 8 and is directed toward the beam splitter 3 again. Then, the light is partly reflected by the beam splitter 3 and applied to the photo-detector 2. That is, the photo-detector 2 mainly receives a part of the reflection light from the object such as the inspection work $SP_s$ and a part of the reflection light from the internal reflection mechanism 8. Further, stray light and the like dispersed within the head 4 due to the light source 1 is also slightly introduced to the photo-detector 2.

As shown in FIG. 3, the role of the reflectance calculation unit 5 is implemented by an information processing unit such as a computer and the like. That is, CPU and peripheral equipments thereof are cooperated with each other according to a program stored in a memory configuring the information processing unit so that the information processing unit functions as the reflectance calculation unit 5. The following describes the details of the function of the reflectance calculation unit 5 as well as the procedural steps of the measurement.

First, explained is a subordinate measurement that is carried out before or after the measurement of the inspection work $SP_s$. This subordinate measurement may be done at a time of initialization, for example, at a time of shipment from a factory. A period for executing this subordinate measurement, i.e., a duration of the period for the subordinate measurement is set within a time period in which variation in the output value of the photo-detector 2 is substantially negligible.

In this subordinate measurement, a dark sample $SP_b$ is placed by an operator at a predetermined sample placing position which is irradiated with the measurement light. The dark sample $SP_b$ is formed of a plate shaped member as shown in FIG. 4 that substantially reflects no light in a wavelength range for use in the measurement.

Figure 6:
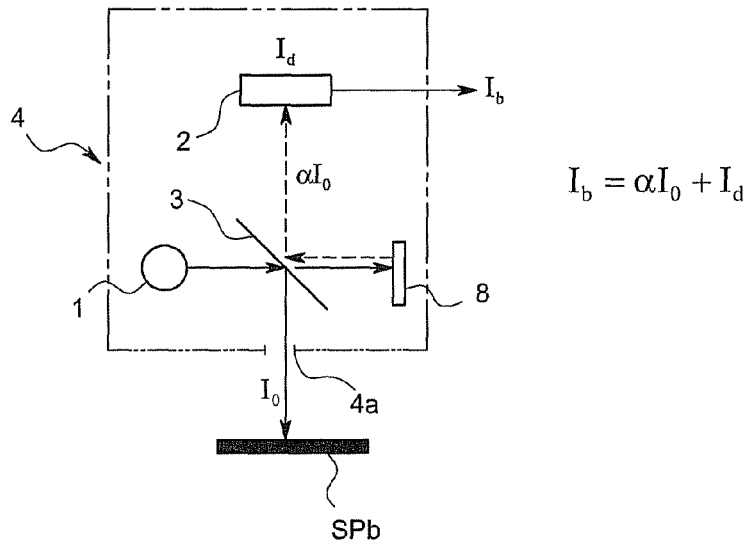
FIG. 6 is a schematic diagram showing a measurement principle in the spectroscopic reflectometer according to the same embodiment.

Then, as shown in FIG. 6, the reflectance calculation unit 5 is operated to calculate the output value of the photo-detector 2, i.e., an output value of each of the sensor elements 22. Thus, each of the output values is stored in a memory as the second output value $I_b$.

Figure 7:
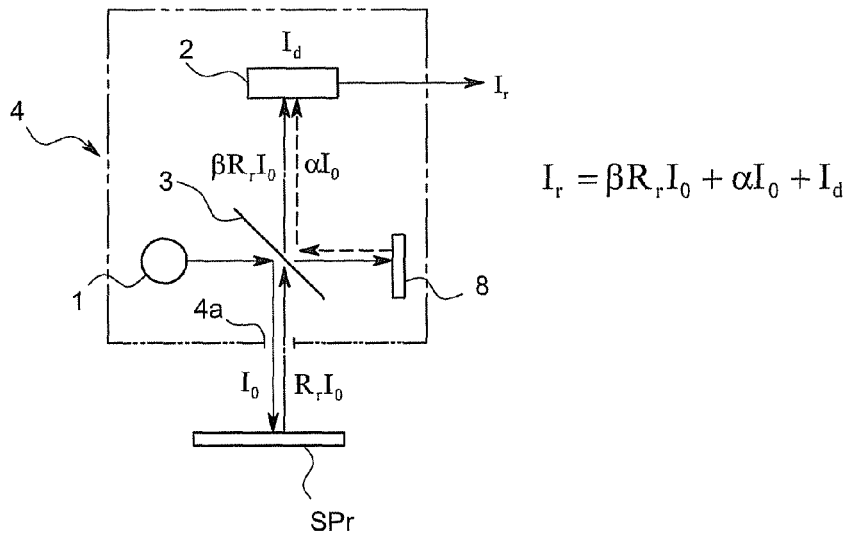
FIG. 7 is a schematic diagram showing a measurement principle in the spectroscopic reflectometer according to the same embodiment.

Next, the operator replaces the dark sample $SP_b$ with a calibration sample $SP_r$ which is placed at the sample placing position. Then, the reflectance calculation unit 5 obtains the output value of the photo-detector 2, i.e., the output value of each of the sensor elements 22 as shown in FIG. 7. Each of the obtained output values is stored in the memory as the third output value $I_r$. It is noted here that the calibration sample $SP_r$ is a plate shaped sample having a known light reflectance.

Meanwhile, the reflectance calculation unit 5 calculates the first output value Id that is an output value of the photo-detector 2 in a state of substantially no light being introduced. Specifically, the offset output value of each of the sensor elements 22 is obtained based on the output value of each of the masked sensor elements 22' so that each of the offset values is stored in the memory as the first output value $I_d$.

The above is the subordinate measurement. It is note here that the order of obtaining a series of the output values $I_b$, $I_r$ and $I_d$ is optional. It is also necessary that the light source 1 should be previously lighted on before carrying out the subordinate measurement to make the light intensity to be in a fully stable condition.

Next, the following describes the main measurement for measuring the inspection work $SP_s$. A period for carrying out the main measurement, i.e., the duration of the main measurement period is set to be within a time period in which the variation in the output value of the photo-detector 2 is substantially negligible, similarly to the case of the subordinate measurement.

Figure 9:
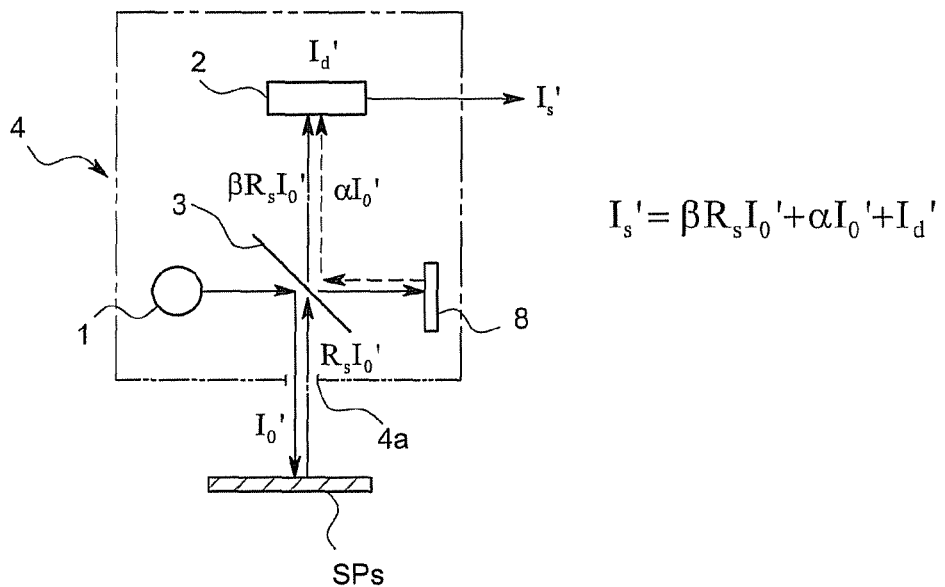
FIG. 9 is a schematic diagram showing a measurement principle in the spectroscopic reflectometer according to the same embodiment.

In this main measurement, the inspection work $SP_s$ is placed by an operator at the predetermined sample placing position. Then, the reflectance calculation unit 5 is operated to calculate the output value of the photo-detector 2, i.e., the output value of each of the sensor elements 22 as shown in FIG. 9. Thus, each of the output values is stored in the memory as the sixth output value M.

Figure 8:
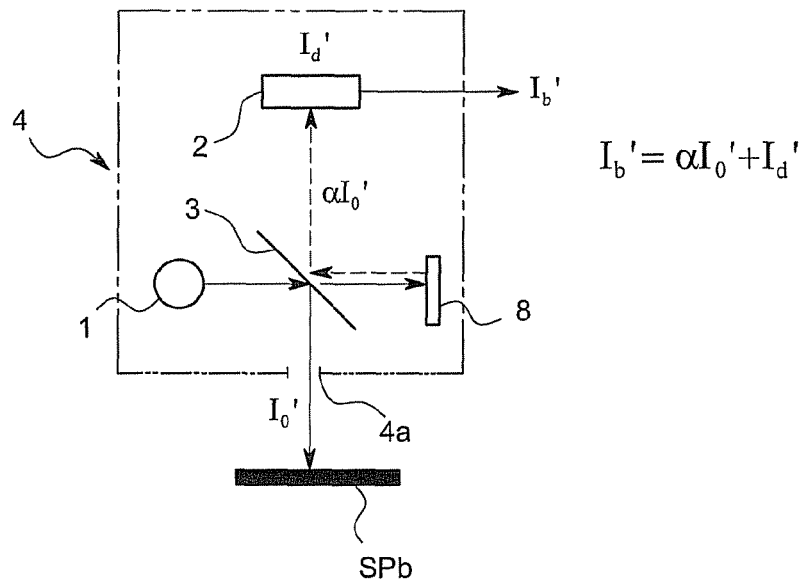
FIG. 8 is a schematic diagram showing a measurement principle in the spectroscopic reflectometer according to the same embodiment.

Next, the operator replaces the inspection work $SP_s$ with the dark sample $SP_b$ which is placed at the sample placing position. Then, as shown in FIG. 8, the reflectance calculation unit 5 obtains the output value of each of the sensor elements 22, and each of the obtained output values is stored in the memory as the fifth output value $I_b'$.

Further, the reflectance calculation unit 5 calculates the offset output value of each of the sensor elements 22 based on the output value of each of the masked sensor elements 22' so that each of the offset values is stored in the memory as the fourth output value $I_d'$, similarly to the case of the subordinate measurement.

The main measurement is completed in this manner. It is noted here that the order of obtaining a series of the output values $I_s'$, $I_b'$ and $I_d'$ is optional. It is also necessary that the light source 1 should be previously lighted on so that the light intensity thereof is kept in a fully stable condition during the period of the main measurement.

Next, the reflectance calculation unit 5 calculates the light reflectance of the inspection work SP, every wavelength based on each of the output values $I_s'$, $I_r$, $I_b$, $I_d$, $I_b'$ and $I_d'$ measured in the main and subordinate measurements. The calculating equation is as follows:

$$R_s = \frac{(I'_s - I'_b)(I_b - I_d)}{(I'_b - I'_d)(I_r - I_b)} R_r \quad \text{[Equation 2]}$$

The reason why this calculating equation (Equation 2) is derived is explained below. The second output value $I_b$ that is the output value obtained from the dark sample $SP_b$ in the subordinate measurement, is a sum of the light intensity of the measurement light that is transmitted and reflected through or by the beam splitter 3, the internal reflection mechanism 8, the inner wall of the head 4 and the like and guided to the photodetector 2 (specifically, one sensor element 22 since the explanation is made regarding one wavelength here) in addition to the first output value Id which is the offset output value of the sensor element 22 in the subordinate measurement. Accordingly, the second output value $I_b$ is represented by Equation 3 (see FIG. 6).

$$I_b = \alpha I_0 + I_d | \quad \text{[Equation 3]}$$

Herein, α denotes an attenuation factor of the measurement light due to undergoing transmission and reflection through or by the beam splitter 3, the internal reflection mechanism 8, the inner wall of the head 4 and the like and is a constant value peculiar to the head 4 without variation in time basis. Io denotes a light intensity of the measurement light at the time of subordinate measurement.

Meanwhile, the third output value $I_r$ that is an output value obtained in the subordinate measurement of the calibration sample $SP_r$ is a sum of the measurement value $I_b$ of the dark sample $SP_b$ in addition to the light intensity of the reflection light that is reflected by the calibration sample $SP_r$ and transmitted through the beam splitter 3 to be guided to the sensor element 22. Accordingly, the third output value $I_r$ is represented by Equation 4 (see FIG. 7).

$$I_r + = \beta R_r I_0 + I_b = \beta R_r I_0 + \alpha I_0 + I_d | \quad \text{[Equation 4]}$$

Herein, β denotes an attenuation factor of the measurement light due to undergoing transmission and reflection through or by the beam splitter 3, the calibration sample $SP_r$, the inner wall of the head 4 and the like and is a constant value peculiar to the head 4 without variation in time basis. $R_r$ denotes a reflectance of the calibration sample $SP_r$ with respect to a light of the corresponding wavelength. $I_0$ denotes a light intensity of the measurement light at the time of subordinate measurement.

If $I_0$ is deleted from these Equations 3 and 4, the following Equation 5 is obtained.

$$\frac{\alpha}{\beta} = \frac{I_b - I_d}{I_r - I_b} R_r \Big| \quad \text{[Equation 5]}$$

On the other hand, the fifth output value $I_b'$ that is an output value obtained in the main measurement of the dark sample $SP_b$ is represented by Equation 6 (see FIG. 8).

$$I_b' = \alpha I_0' + I_d' | \quad \text{[Equation 6]}$$

Herein, $I_0'$ denotes a light intensity of the measurement light at the time of main measurement, and $I_d'$ denotes an offset output value of the sensor element 22 at the time of main measurement.

Further, the sixth output value $I_s'$ that is an output value of the sensor element 22 obtained in measuring the inspection work $SP_s$ is a sum of the measurement value $I_b'$ of the dark sample $SP_b$ in addition to the light intensity of the reflection light that is reflected by the inspection work $SP_s$ and transmitted through beam splitter 3 to be guided to the sensor element 22. Accordingly, the sixth output value $I_s'$ is represented by Equation 7.

$$I_s' = \beta R_s I_0' + I_b' = \beta R_s I_0' + \alpha I_0' + I_d' | \quad \text{[Equation 7]}$$

If $I_0'$ is deleted from these Equations 6 and 7, the following Equation 8 is obtained.

$$\frac{\alpha}{\beta} = \frac{I_b' - I_d'}{I_s' - I_b'} R_s \quad \text{[Equation 8]}$$

Thus, since α, β are considered to be constant values peculiar to the head, the values of Equations 5 and 8 are equal, and hence Equation 2 mentioned above is derived from these Equations 5 and 8.

Therefore, according to the present embodiment, since the measurement of the calibration sample $SP_r$ is required merely at least one time only in the subordinate measurement, it becomes unnecessary to measure the calibration sample $SP_r$ in the main measurement. And in consideration that the measurement of the calibration sample $SP_r$ subject to many constraints and troubles such that the measurement conditions must be made equal with respect to the inspection work compared to the measurement of the dark sample $SP_b$, it becomes possible to remarkably reduce the trouble and time for measurement compared to those of conventional products where the measurement of the calibration sample $SP_r$ has been carried out every time the inspection work $SP_s$ is measured, i.e., at the time of main measurement.

The reason why the measurement of the calibration sample $SP_r$ can be omitted at the time of main measurement as described above is because the first output value that is an offset amount which is not caused by the light source 1 is measured to be considered in separation from an offset amount which is caused by the light source 1. That is, it becomes possible for the first time by obtaining a factor, i.e., a ratio between and α and β, which is peculiar to the head 4 without variation in time basis although the factor is not present on the appearance of Equation 2 for calculating the light reflectance.

The specific feature of the present invention also resides in the fact that the offset amount caused by the light source 1 is not reduced as in the conventional way but the value thereof is aggressively increased by the internal reflection mechanism 8. By this arrangement, it becomes possible to correctly obtain the ratio between and α and β. In theoretic, the ratio between and α and β may be obtained by utilizing stray light such as reflection light by the inner wall of the head 4 without aggressively providing an exclusive internal reflection mechanism 8. However, if so, such an aspect is somewhat inferior in measurement accuracy compared to the present embodiment.

Second Embodiment

The following describes a second embodiment of the present invention.

Figure 10:
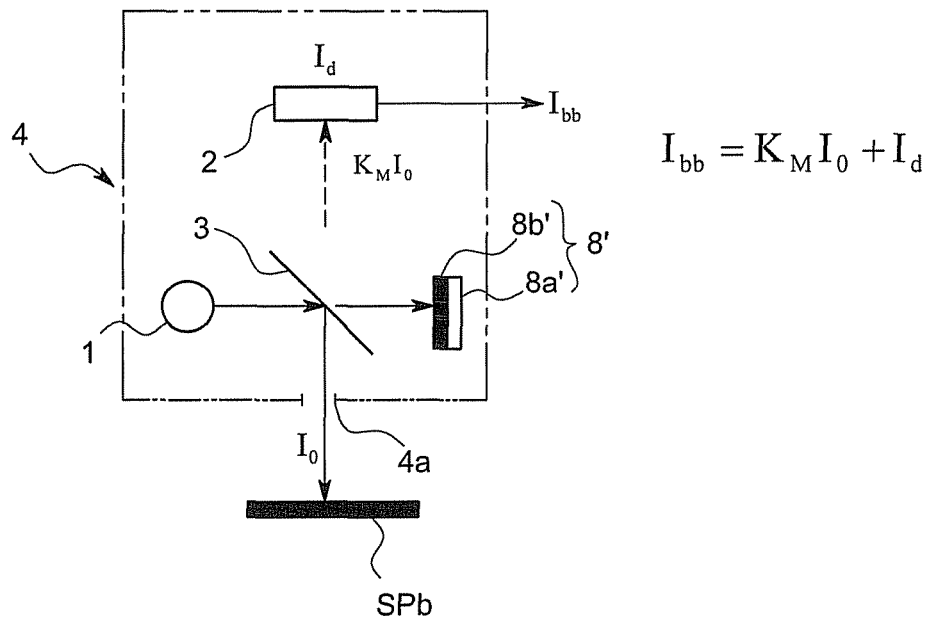
FIG. 10 is a schematic diagram showing a measurement principle of a spectroscopic reflectometer according to a second embodiment of the present invention.

In this second embodiment, as shown in FIG. 10 etc., an internal reflection mechanism 8' is different from that of the first embodiment. Specific, the internal reflection mechanism 8' in the present embodiment includes, for example, a non-reflective member 8b' which reflects substantially no light and a reflective member 8a' having a known and predetermined light reflectance. The internal reflection mechanism 8' has a configuration such that, the non-reflective member 8b' is so provided as to be slidable between a position covering a surface of the reflective member 8a' and a position exposing the surface of the reflective member 8a' so that the light reflectance thereof can be changed between different two values of a first value (value 0) and a second value (predetermined value other than 0). However, the first value may not be 0.

Figure 11:
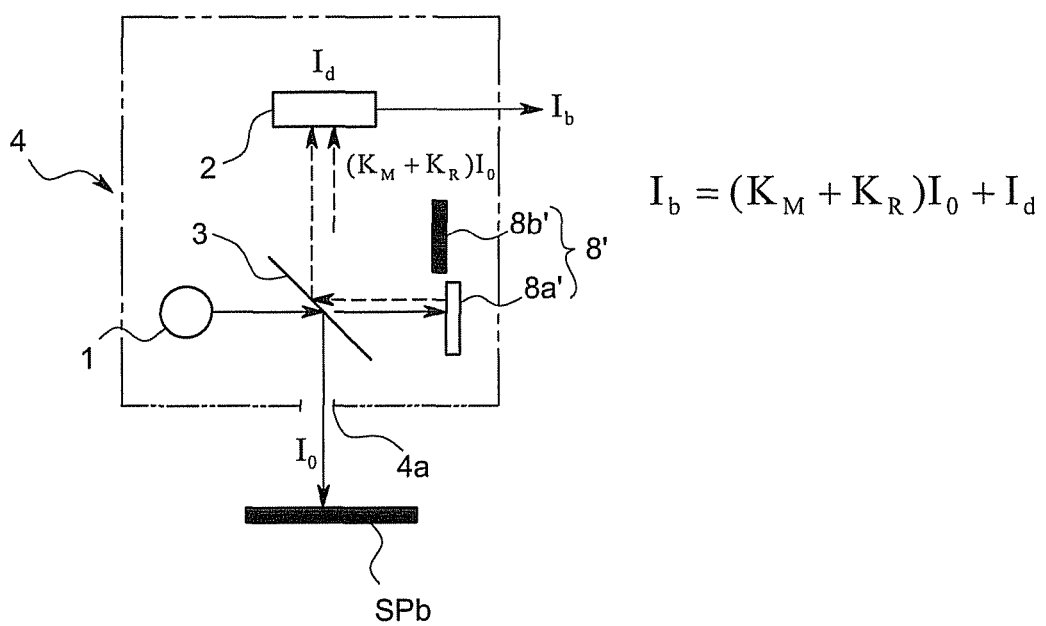
FIG. 11 is a schematic diagram showing a measurement principle in the spectroscopic reflectometer according to the same embodiment.

Thus, when a dark sample $SP_b$ is placed by an operator at a sample placing position of the head 4 in the subordinate measurement as described above, the reflectance calculation unit 5 operates the non-reflective member 8b' to cover the reflective member 8a' as shown in FIG. 10, so that the reflectance of the internal reflection mechanism 8' is set to the first value. Then, the reflectance calculation unit 5 obtains the output value of the photo-detector 2 (i.e., output value of each sensor element 22) and each of the obtained output values is stored in the memory as a first output value $I_{bb}$. Next, the reflectance calculation unit 5 moves the non-reflective member 8b' to expose the surface of the reflective member 8a' as shown in FIG. 11, so that the reflectance of the internal reflection mechanism 8' is set to the second value. Then, the reflectance calculation unit 5 obtains the output value of the photo-detector 2 (i.e., output value of each sensor element 22) and each of the obtained output values is stored in the memory as a second output value $I_b$).

Figure 12:
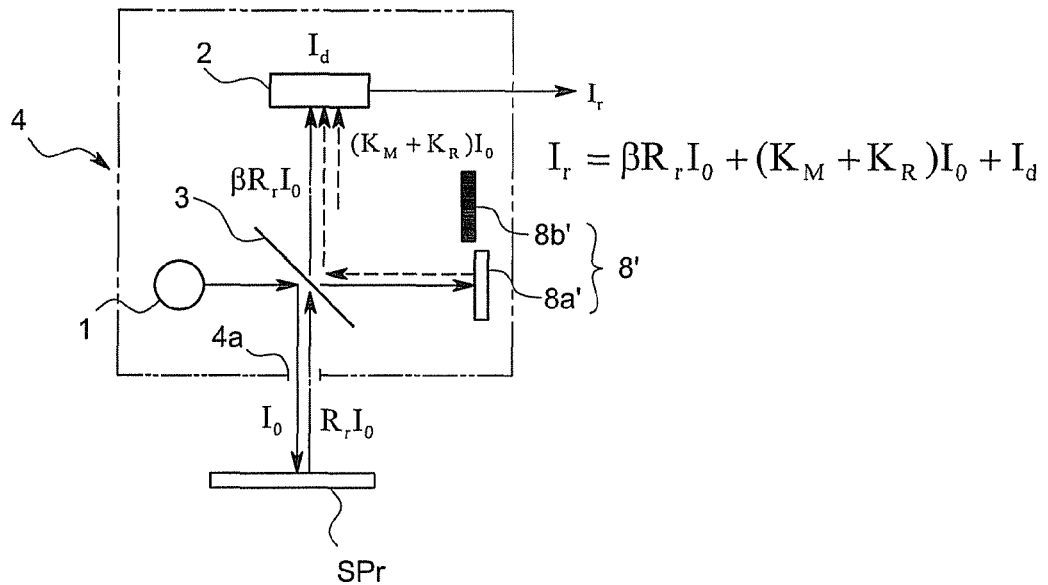
FIG. 12 is a schematic diagram showing a measurement principle in the spectroscopic reflectometer according to the same embodiment.

Next, when a calibration sample $SP_r$ is placed by an operator at the sample placing position as shown in FIG. 12, the reflectance calculation unit 5 obtains an output value of the photo-detector 2 (i.e., output value of each sensor element 22) under the condition that the reflectance of the internal reflection mechanism 8' is set to the second value. Then, each of the obtained output values is stored in the memory as a third output value $I_r$.

The above is the subordinate measurement. It is note here that the order of obtaining a series of the output values $I_{bb}$, $I_b$ and $I_r$ is optional. It is also necessary that the light source 1 should be previously lighted on before carrying out the subordinate measurement to make the light intensity to be in a fully stable condition.

Next, the main measurement is carried out for measuring the inspection work $SP_s$. The procedure of this main measurement is almost the same as that of the subordinate measurement except that the inspection work $SP_s$ is placed at the sample placing position instead of the calibration sample $SP_r$.

Figure 13:
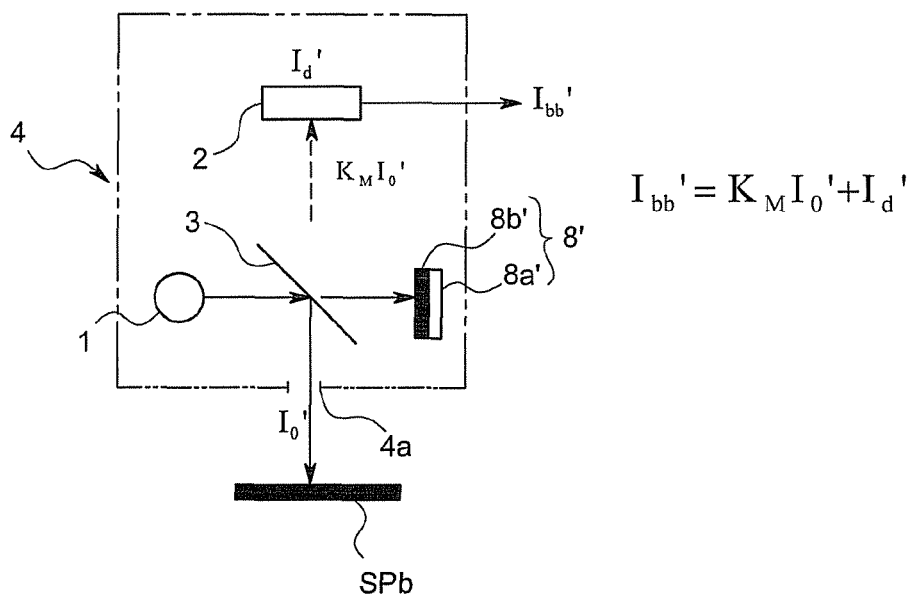
FIG. 13 is a schematic diagram showing a measurement principle in the spectroscopic reflectometer according to the same embodiment.

Specifically, as shown in FIG. 13, when the dark sample $SP_b$ is placed by an operator at the sample placing position, the reflectance calculation unit 5 sets the reflectance of the internal reflection mechanism 8' to the first value and obtains the output value of the photo-detector 2 (i.e., output value of each sensor element 22). Then, each of the obtained output values is stored in the memory as a fourth output value $I_{bb}'$. Next, the reflectance calculation unit 5 sets the reflectance of the internal reflection mechanism 8' to the second value and obtains the output value of the photo-detector 2 (i.e., output value of each sensor element 22). Then, each of the obtained output values is stored in the memory as a fifth output value $I_b'$.

Next, when the inspection work SP, is placed beneath the head 4 by an operator, the reflectance calculation unit 5 obtains the output value of the photo-detector 2 (i.e., output value of each sensor element 22) under the condition that the reflectance of the internal reflection mechanism 8' is set to the second value. Then, each of the obtained output values is stored in the memory as a sixth output value $I_s'$.

The main measurement is completed in this manner. It is noted here that the order of obtaining a series of the output values $I_s'$, $I_b'$ and $I_{bb}'$ is optional. It is also necessary that the light source 1 should be previously lighted on so that the light intensity thereof is kept in a fully stable condition during the period of the main measurement.

Next, the reflectance calculation unit 5 calculates the light reflectance of the inspection work SP, every wavelength based on each of the output values $I_r$, $I_b$, $I_{bb}$, $I_s'$, $I_b'$ and $I_{bb}'$ measured in the main and subordinate measurements. The calculating equation is as follows:

$$R_s = \frac{(I_s' - I_b')(I_b - I_{bb})}{(I_b' - I_{bb}')(I_r - I_b)} R_r \qquad \text{[Equation 9]}$$

The reason why this calculating equation (Equation 9) is derived is explained below. The first and second output values $I_{bb}$ and $I_b$ that are the output value obtained from the dark sample $SP_b$ when the reflectance of the internal reflection mechanism 8' is set to the first and second values, respectively in the subordinate measurement, is a sum of the light intensity of the measurement light that is transmitted and reflected through or by the beam splitter 3, the internal reflection mechanism 8', the inner wall of the head 4 and the like and guided to the photo-detector 2 (specifically, one sensor element 22 since the explanation is made regarding one wavelength here) in addition to the offset output value $I_d$ of the sensor element 22 in the subordinate measurement. Accordingly, the first and second output values $I_{bb}$ and $I_b$ are represented by Equations 10 and 11 (see FIGS. 10 and 11).

$$I_{bb} = K_M I_0 + I_d \qquad \text{[Equation 10]}$$

$$I_b = (K_M + K_R) I_0 + I_d \qquad \text{[Equation 11]}$$

Herein, $K_M$ denotes an attenuation factor of the measurement light when the reflectance of the internal reflection mechanism 8' is the first value (0) which represents the attenuation factor of the measurement light due to undergoing transmission and reflection through or by the beam splitter 3, the inner wall of the head 4 and the like except the internal reflection mechanism 8'. $K_R$ denotes an attenuation factor of the measurement light in the internal reflection mechanism 8' when the reflectance of the internal reflection mechanism 8' is set to the second value. These $K_M$ and $K_R$ are constant values peculiar to the head 4 without variation in time basis.

Since the reflectance of the internal reflection mechanism 8' is set to the second value, the output value in the subordinate measurement of the calibration sample $SP_r$, i.e., the third output value $I_r$ is a sum of the measurement value $I_b$ of the dark sample $SP_b$ in addition to the light intensity of the reflection light that is reflected by the calibration sample $SP_r$ and transmitted through the beam splitter 3 to be guided to the sensor element 22. Accordingly, the third output value $I_r$ is represented by Equation 12 (see FIG. 12).

$$I_r = \beta R_r I_0 + I_b \qquad \text{[Equation 12]}$$

If $I_c$, and $K_M$ are deleted from these Equations 10 to 12, the following Equation 13 is derived.

$$\frac{K_R}{\beta} = \frac{I_b - I_{bb}}{I_r - I_b} R_r \qquad \text{[Equation 13]}$$

Figure 14:
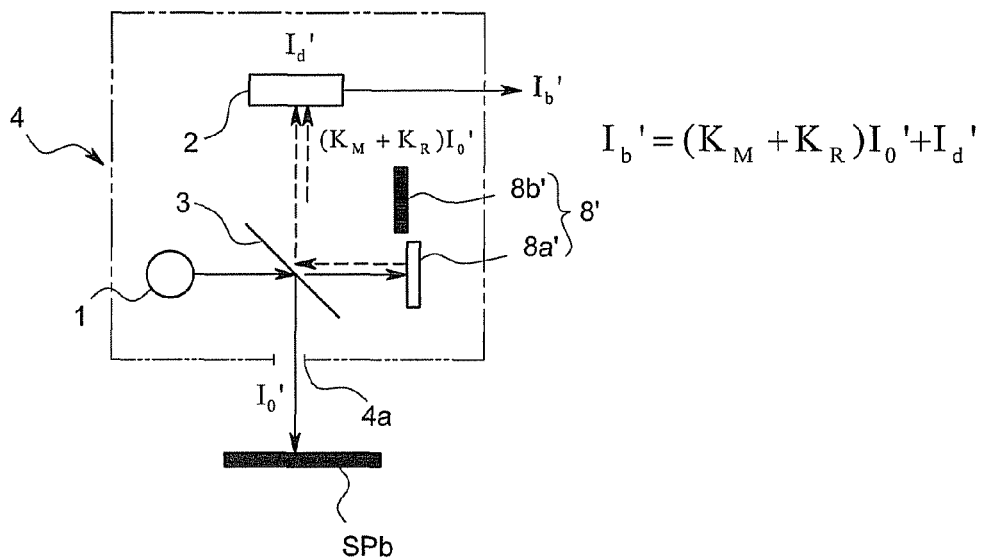
FIG. 14 is a schematic diagram showing a measurement principle in the spectroscopic reflectometer according to the same embodiment.
Figure 15:
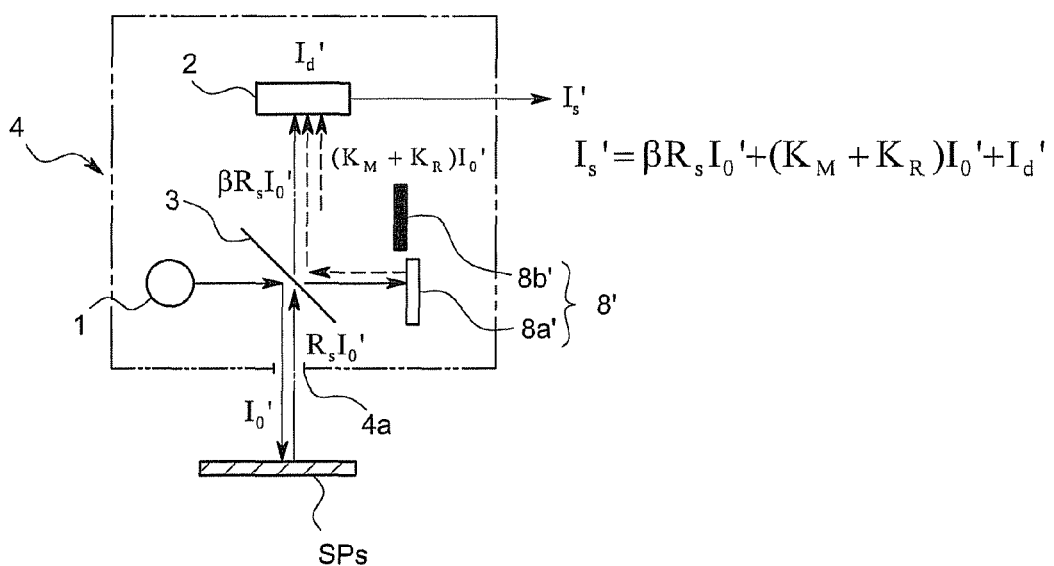
FIG. 15 is a schematic diagram showing a measurement principle in the spectroscopic reflectometer according to the same embodiment.

On the other hand, the fourth output value $I_{bb}'$, the fifth output value $I_b'$ that are output values obtained in the main measurement of the dark sample $SP_b$ and the sixth output value $I_s'$ obtained in the measurement of the inspection work SP, are represented by Equations 14 to 16, respectively (see FIGS. 13 to 15).

$$I_{bb}' = K_M I_0' + I_d' \quad \text{[Equation 14]}$$

$$I_b' = (K_M + K_R) I_0' + I_d' \quad \text{[Equation 15]}$$

$$I_s' = \beta R_s I_0' + I_b' \quad \text{[Equation 16]}$$

Then, the following Equation 17 is derived from these Equations.

$$\frac{K_R}{\beta} = \frac{I_b' - I_{bb}'}{I_s' - I_b'} R_s \Big| \quad \text{[Equation 17]}$$

In the meanwhile, since 13 and $K_R$ are constant, if $R_r$ is calculated, Equation 18 is obtained as follows:

$$R_s = \frac{(I_s' - I_b')(I_b - I_{bb})}{(I_b' - I_{bb}')(I_r - I_b)} R_r \Big| \quad \text{[Equation 18]}$$

and hence Equation 9 is derived.

A method of measuring the reflectance in the second embodiment is to be summarized as following.
[Subordinate Measurement]
Measurement 1 of dark sample (see FIG. 10)
 Setting internal reflection mechanism to first value
 Obtaining first output value $I_{bb}$
Measurement 2 of dark sample (see FIG. 11)
 Setting internal reflection mechanism to second value
 Obtaining second output value $I_b$
Measurement of calibration sample (see FIG. 12)
 Setting internal reflection mechanism to second value
 Obtaining third output value $I_r$
[Main Measurement]
Measurement 1 of dark sample (see FIG. 13)
 Setting internal reflection mechanism to first value
 Obtaining fourth output value $I_{bb}'$
Measurement 2 of dark sample
 Setting internal reflection mechanism to second value (see FIG. 14)
 Obtaining fifth output value $I_b'$
Measurement of inspection work (see FIG. 15)
 Setting internal reflection mechanism to second value
 Obtaining sixth output value $I_s'$
[Calculation of Reflectance of Inspection Work]
 Done by the Equation 9.

Another Embodiment

The following describes another embodiment of the present invention. It is noted that, since the configuration of the equipment is the same as the second embodiment, the explanation thereof is omitted here.

In the second embodiment, $K_R/\beta$ are obtained in the subordinate and main measurements and the reflectance $R_s$ of the inspection work $SP_s$ is calculated based on the fact that these are in the relation of being equal to each other.

Whereas, there are four kinds of methods for obtaining $K_R/\beta$ mentioned above including a method in the second embodiment in the subordinate measurement and the main measurement, respectively. The reflectance $R_s$ of the inspection work $SP_s$ can be calculated in any combination of these methods. That is, as a method of calculating the reflectance of the inspection work $SP_s$, there are 16 ways in total including the method in the second embodiment, and any of them can be used.

Therefore, the methods of obtaining $K_R/\beta$ in the subordinate and main measurements excluding the method in the second embodiment are respectively explained as follows.

Figure 16:
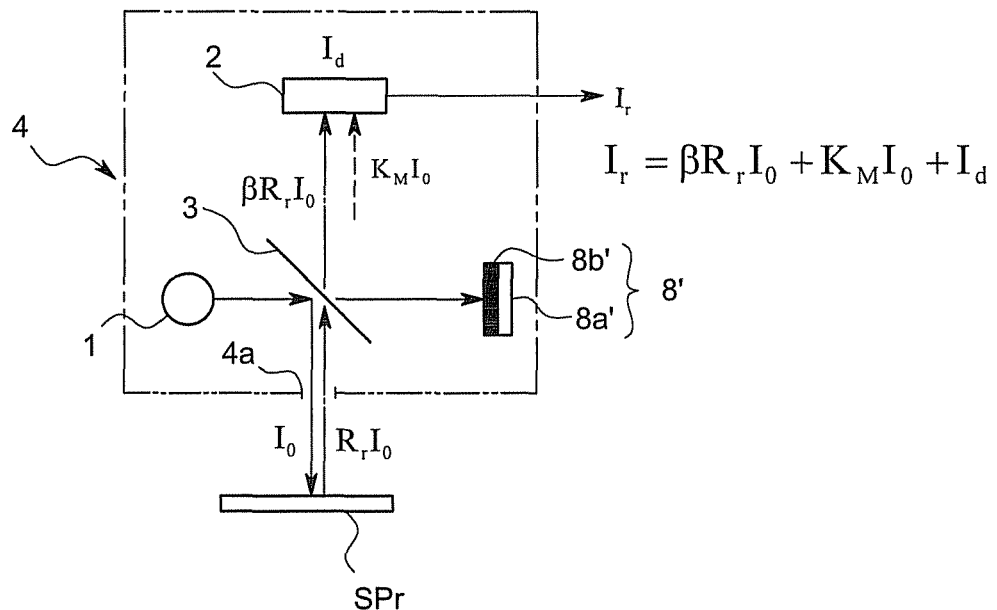
FIG. 16 is a schematic diagram showing a measurement principle of a spectroscopic reflectometer according to another embodiment of the present invention.

The following three kinds are available in the subordinate measurement.
[Calculation Method 1 of $K_R/\beta$ in Subordinate Measurement]
Measurement 1 of dark sample (see FIG. 10)
 Setting internal reflection mechanism to first value
 Obtaining first output value $I_{bb}$
Measurement 2 of dark sample (see FIG. 11)
 Setting internal reflection mechanism to second value
 Obtaining second output value $I_b$
Measurement of calibration sample (see FIG. 16)
 Setting internal reflection mechanism to first value
 Obtaining third output value $I_r$
$K_R/\beta$ is calculated from each of the output values (Equation 19).

$$\frac{K_R}{\beta} = \frac{I_b - I_{bb}}{I_r - I_{bb}} R_r \quad \text{[Equation 19]}$$

Figure 18:
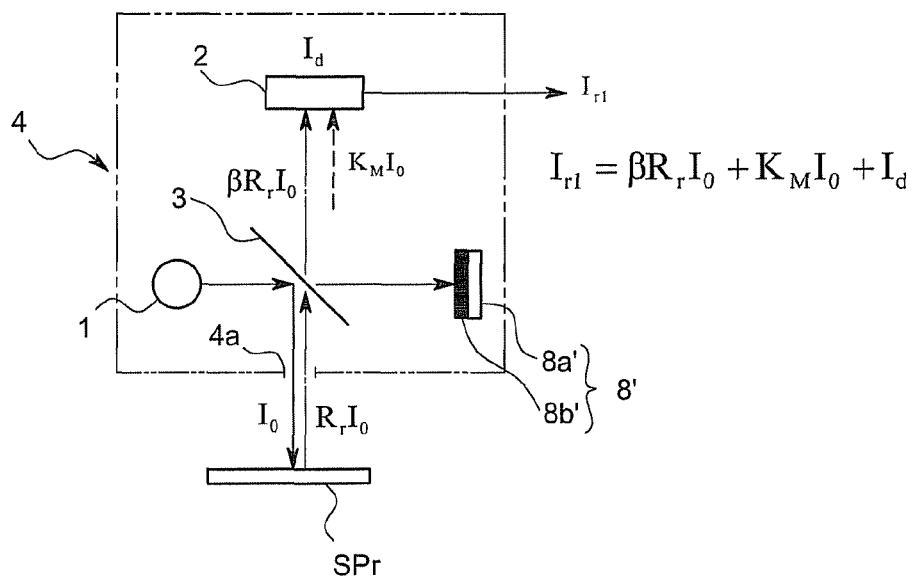
FIG. 18 is a schematic diagram showing a measurement principle of the spectroscopic reflectometer according to the same embodiment.
Figure 19:
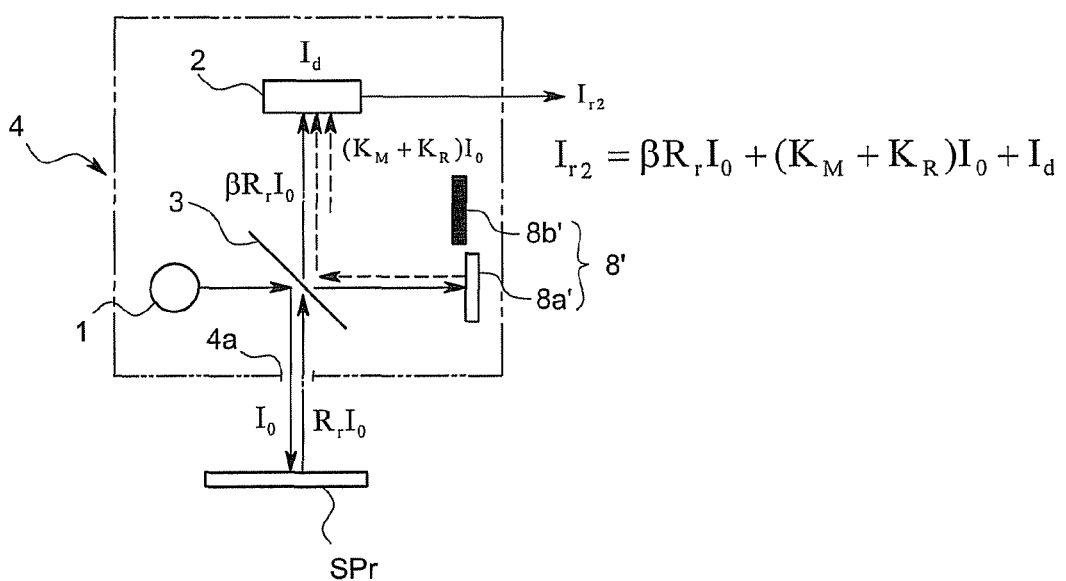
FIG. 19 is a schematic diagram showing a measurement principle in the spectroscopic reflectometer according to the same embodiment.

[Calculation Method 2 of $K_R/\beta$ in Subordinate Measurement]
Measurement of dark sample (see FIG. 10)
 Setting internal reflection mechanism to first value
 Obtaining first output value $I_{bb}$
Measurement 1 of calibration sample (see FIG. 18)
 Setting internal reflection mechanism to first value
 Obtaining second output value $I_{r1}$
Measurement 2 of calibration sample (see FIG. 19)
 Setting internal reflection mechanism to second value
 Obtaining third output value $I_{r2}$
$K_R/\beta$ is calculated from each of the output values (Equation 20).

$$\frac{K_R}{\beta} = \frac{I_{r2} - I_{r1}}{I_{r1} - I_{bb}} R_r \Big| \quad \text{[Equation 20]}$$

[Calculation Method 3 of $K_R/\beta$ in Subordinate Measurement]
Measurement of dark sample (see FIG. 11)
 Setting internal reflection mechanism to second value
 Obtaining first output value $I_b$
Measurement 1 of calibration sample (see FIG. 18)
 Setting internal reflection mechanism to first value
 Obtaining second output value $I_{r1}$
Measurement 2 of calibration sample (see FIG. 19)
 Setting internal reflection mechanism to second value
 Obtaining third output value $I_{r2}$
$K_R/\beta$ is calculated from each of the output values (Equation 21).

$$\frac{K_R}{\beta} = \frac{I_{r2} - I_{r1}}{I_{r2} - I_b} R_r \Big| \quad \text{[Equation 21]}$$

Figure 17:
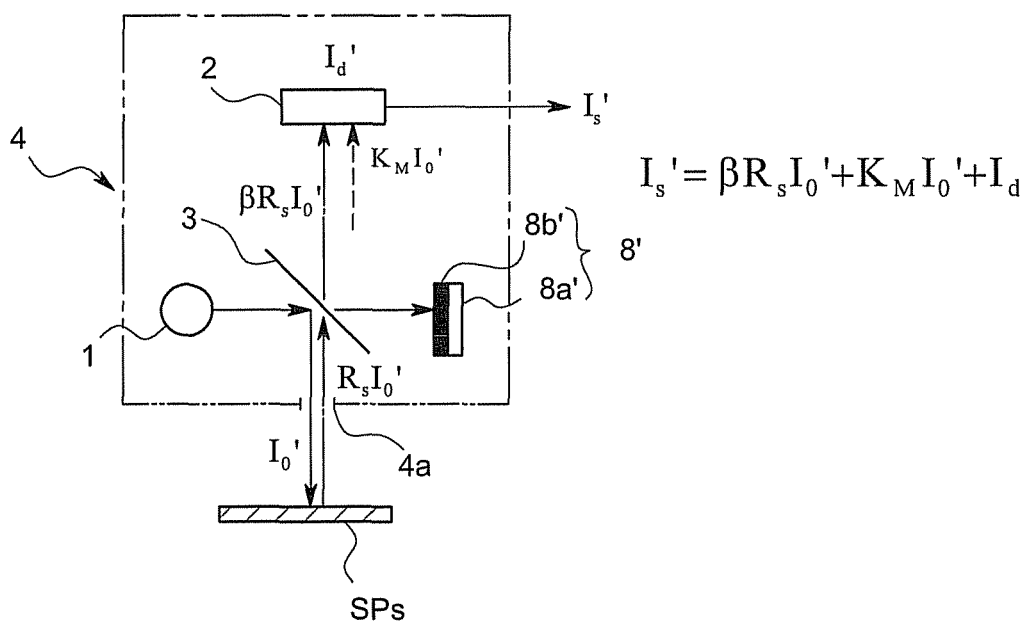
FIG. 17 is a schematic diagram showing a measurement principle in the spectroscopic reflectometer according to the same embodiment.

The following three kinds are available in the main measurement.
[Calculation Method 1 of $K_R/\beta$ in Main Measurement]
Measurement 1 of dark sample (see FIG. 13)
 Setting internal reflection mechanism to first value
 Obtaining fourth output value $I_{bb}'$ Measurement 2 of dark sample
  Setting internal reflection mechanism to second value (see FIG. 14)
  Obtaining fifth output value $I_b'$
Measurement of inspection work (see FIG. 17)
  Setting internal reflection mechanism to first value
  Obtaining sixth output value $I_s'$
$K_R/\beta$ is calculated from each of the output values (Equation 22).

$$\frac{K_R}{\beta} = \frac{I_b' - I_{bb}'}{I_s' - I_{bb}'} R_s \quad \text{[Equation 22]}$$

Figure 20:
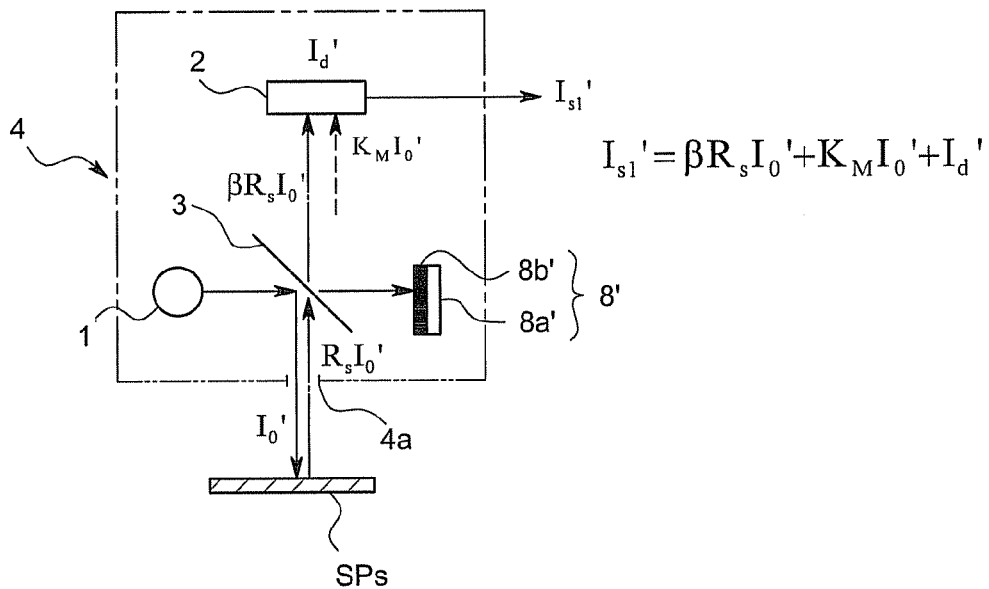
FIG. 20 is a schematic diagram showing a measurement principle in the spectroscopic reflectometer according to the same embodiment.
Figure 21:
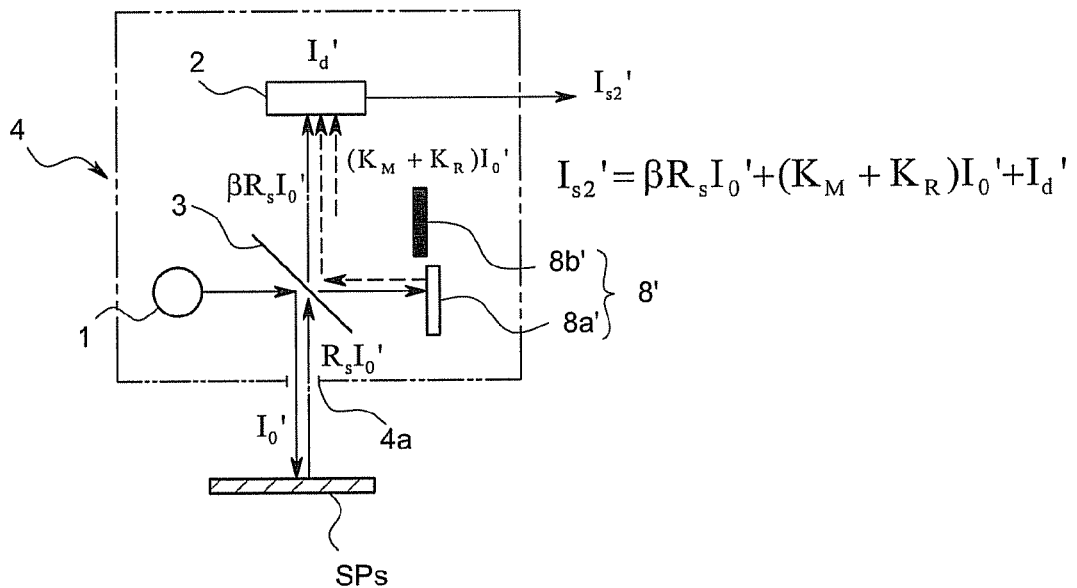
FIG. 21 is a schematic diagram showing a measurement principle in the spectroscopic reflectometer according to the same embodiment.

[Calculation Method 2 of $K_R/\beta$ in Main Measurement]
Measurement of dark sample (see FIG. 13)
  Setting internal reflection mechanism to first value
  Obtaining fourth output value $I_{bb}'$
Measurement 1 of inspection work (see FIG. 20)
  Setting internal reflection mechanism to first value
  Obtaining fifth output value $I_{s1}'$
Measurement 2 of inspection work (see FIG. 21)
  Setting internal reflection mechanism to second value
  Obtaining sixth output value $I_{s2}'$
$K_R/\beta$ is calculated from each of the output values (Equation 23).

$$\frac{K_R}{\beta} = \left|\frac{I_{s2}' - I_{s1}'}{I_{s1}' - I_{bb}'} R_s\right| \quad \text{[Equation 23]}$$

[Calculation Method 3 of $K_R/\beta$ in Main Measurement]
Measurement of dark sample (see FIG. 14)
  Setting internal reflection mechanism to second value
  Obtaining fourth output value $I_b'$
Measurement 1 of inspection work (see FIG. 20)
  Setting internal reflection mechanism to first value
  Obtaining fifth output value $I_{s1}'$
Measurement 2 of inspection work (see FIG. 21)
  Setting internal reflection mechanism to second value
  Obtaining sixth output value $I_{s2}'$ $K_R/\beta$ is calculated from each of the output values (Equation 24).

$$\frac{K_R}{\beta} = \frac{I_{s2}' - I_{s1}'}{I_{s2}' - I_b'} R_s \quad \text{[Equation 24]}$$

As described above, there are four kinds of methods calculating $K_R/\beta$ using Equations 13, 19, 20 and 21 in the subordinate measurement and also four kinds of methods using Equations 17, 22, 23 and 24 in the main measurement. The light reflectance Rs can be obtained by combination of these methods and all of them are represented by Equations 25 to 40 as follows.

Equation 13 × Equation 17
(same as embodiment 2)

$$R_s = \frac{(I_s' - I_b')(I_b - I_{bb})}{(I_b' - I_{bb}')(I_r - I_b)} R_r \quad \text{[Equation 25]}$$

Equation 13 × Equation 22

$$R_s = \frac{I_s' - I_{bb}'}{I_b' - I_{bb}'} \cdot \frac{I_b - I_{bb}}{I_r - I_b} R_r \quad \text{[Equation 26]}$$

Equation 13 × Equation 23

$$R_s = \left|\frac{I_{s1}' - I_{bb}'}{I_{s2}' - I_{s1}'} \cdot \frac{I_b - I_{bb}}{I_r - I_b} R_r\right| \quad \text{[Equation 27]}$$

Equation 13 × Equation 24

$$R_s = \frac{I_{s2}' - I_b'}{I_{s2}' - I_{s1}'} \cdot \frac{I_b - I_{bb}}{I_r - I_b} R_r \quad \text{[Equation 28]}$$

Equation 19 × Equation 17

$$R_s = \frac{I_s' - I_b'}{I_b' - I_{bb}'} \cdot \frac{I_b - I_{bb}}{I_r - I_{bb}} R_r \quad \text{[Equation 29]}$$

Equation 19 × Equation 22

$$R_s = \frac{I_s' - I_{bb}'}{I_b' - I_{bb}'} \cdot \frac{I_b - I_{bb}}{I_r - I_{bb}} R_r \quad \text{[Equation 30]}$$

Equation 19 × Equation 23

$$R_s = \left|\frac{I_{s1}' - I_{bb}'}{I_{s2}' - I_{s1}'} \cdot \frac{I_b - I_{bb}}{I_r - I_{bb}} R_r\right| \quad \text{[Equation 31]}$$

Equation 19 × Equation 24

$$R_s = \frac{I_{s2}' - I_b'}{I_{s2}' - I_{s1}'} \cdot \frac{I_b - I_{bb}}{I_r - I_{bb}} R_r \quad \text{[Equation 32]}$$

Equation 20 × Equation 17

$$R_s = \frac{I_s' - I_b'}{I_b' - I_{bb}'} \cdot \frac{I_{r2} - I_{r1}}{I_{r1} - I_{bb}} R_r \quad \text{[Equation 33]}$$

Equation 20 × Equation 22

$$R_s = \left|\frac{I_s' - I_{bb}'}{I_b' - I_{bb}'} \cdot \frac{I_b - I_{bb}}{I_r - I_b} R_r\right| \quad \text{[Equation 34]}$$

Equation 20 × Equation 23

$$R_s = \left|\frac{I_{s1}' - I_{bb}'}{I_{s2}' - I_{s1}'} \cdot \frac{I_{r2} - I_{r1}}{I_{r1} - I_{bb}} R_r\right| \quad \text{[Equation 35]}$$

Equation 20 × Equation 24

$$R_s = \left|\frac{I_{s2}' - I_b'}{I_{s2}' - I_{s1}'} \cdot \frac{I_{r2} - I_{r1}}{I_{r1} - I_{bb}} R_r\right| \quad \text{[Equation 36]}$$

Equation 21 × Equation 17

$$R_s = \left|\frac{I_s' - I_b'}{I_b' - I_{bb}'} \cdot \frac{I_{r2} - I_{r1}}{I_{r2} - I_b} R_r\right| \quad \text{[Equation 37]}$$

Equation 21 × Equation 22

$$R_s = \left|\frac{I_s' - I_{bb}'}{I_b' - I_{bb}'} \cdot \frac{I_{r2} - I_{r1}}{I_{r2} - I_b} R_r\right| \quad \text{[Equation 38]}$$

Equation 21 × Equation 23

$$R_s = \left|\frac{I_{s1}' - I_{bb}'}{I_{s2}' - I_{s1}'} \cdot \frac{I_{r2} - I_{r1}}{I_{r2} - I_b} R_r\right| \quad \text{[Equation 39]}$$

Equation 21 × Equation 24

$$R_s = \left|\frac{I_{s2}' - I_b'}{I_{s2}' - I_{s1}'} \cdot \frac{I_{r2} - I_{r1}}{I_{r2} - I_b} R_r\right| \quad \text{[Equation 40]}$$

It is noted that the present invention should not be limited to the embodiments mentioned above.

Figure 22:
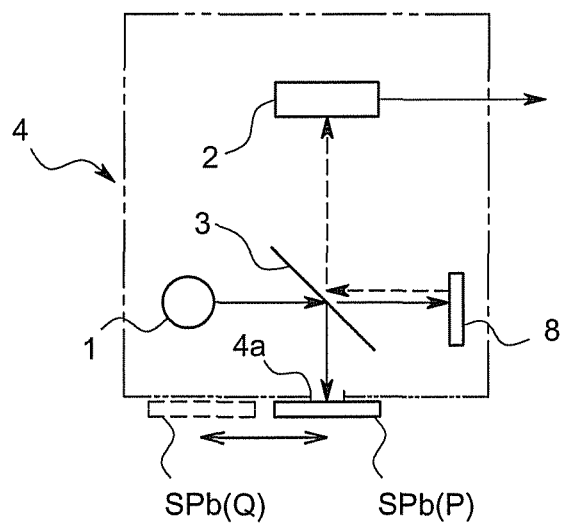
FIG. 22 is a schematic functional diagram of a spectroscopic reflectometer according to further another embodiment of the present invention.

For example, as shown in FIG. 22, the dark sample $SP_b$ may be attached to the head 4 in a manner that the light inlet and outlet port 4a can be opened and closed. With this configuration, it becomes unnecessary to move the head 4 for measuring the dark sample in any of the subordinate and main measurements. Therefore, simplification in structure and reduction in cost can be promoted as a fixed type head 4. Moreover, as shown in FIG. 22, (P) shows an irradiation position that is irradiated with measurement light, and (Q) shows a retraction position that is not irradiated with measurement light. Thus, the dark sample $SP_b$ is slidably annexed to the head 4 between the irradiation position (P) and the retraction position (Q).

Figure 23:
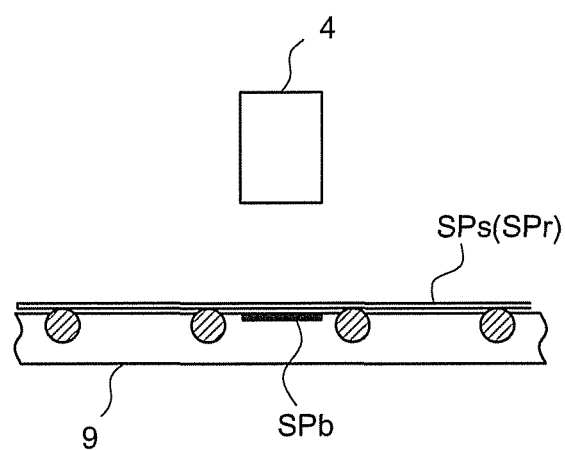
FIG. 23 is a partial section view showing a spectroscopic reflectometer according to further another embodiment of the present invention.

Moreover, as shown in FIG. 23, the dark sample $SP_b$ has been previously fixed to or installed on a base stage 9 so that the inspection work $SP_s$ or the calibration sample $SP_r$ may be placed thereon. In this arrangement, a troublesome operation of detaching the dark sample can be omitted. In addition, the dark sample may be positioned anywhere.

Figure 24:
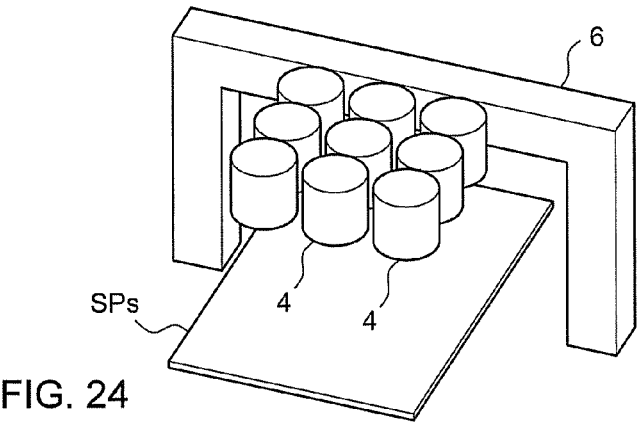
FIG. 24 is a schematic perspective view of a spectroscopic reflectometer according to further another embodiment of the present invention.
Figure 25:
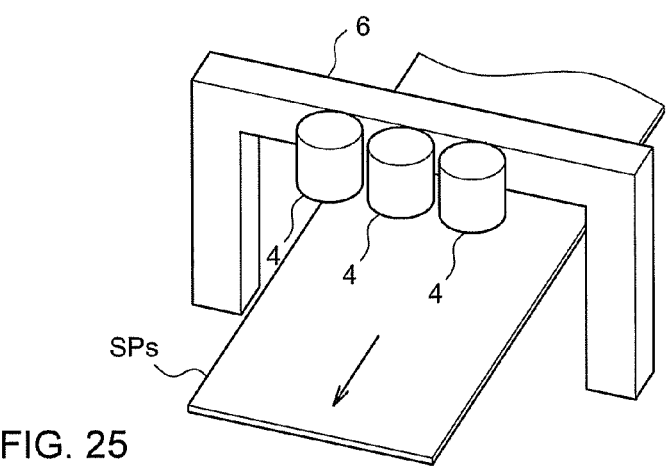
FIG. 25 is a schematic perspective view of a spectroscopic reflectometer according to further another embodiment of the present invention.

As shown in FIGS. 24 and 25, the head 4 is not necessarily one, and two or more heads may be provided. In case of providing a plurality of heads 4, more significant reduction in cost and measurement time can be attained by a manner of fixing the heads 4. FIG. 24 shows an example of arranging the heads 4 in flat plane shaped to be able to measure an area, and FIG. 25 shows an example of arranging the heads 4 in line shaped so that the inspection work $SP_s$ is moved in a direction perpendicular to a line direction to be scanned. Thus, in the case of solar cells and LC flat panels where the inspection work flows, since there is no time for the heads to be moved, the fixed type thereof is particularly preferred.

Figure 26:
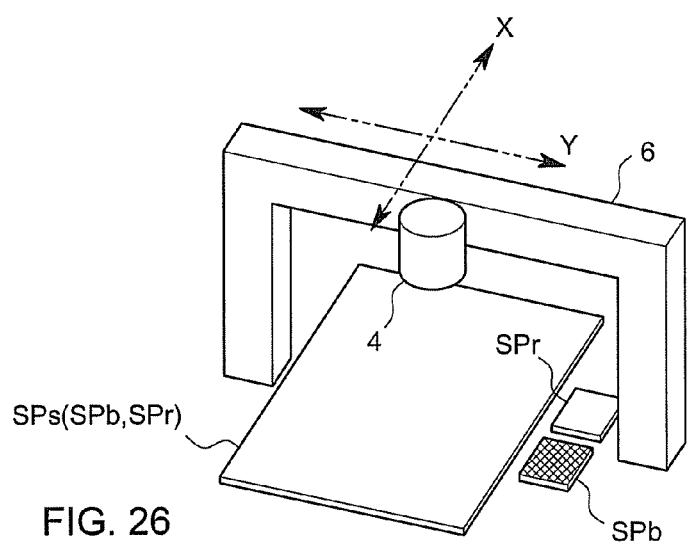
FIG. 26 is a schematic perspective view of a spectroscopic reflectometer according to further another embodiment of the present invention.

As shown in FIG. 26, the head 4 may be moved in horizontal two axes (X axis, Y axis) directions and further a Z direction may be added so that the head 4 can be moved in the three axes directions.

Further, the reflectance calculation unit is not necessarily provided, and an operator or a measurer may calculate the light reflectance by human calculation based on, for example, each of the output values.

In addition, in the embodiments, although the spectral function is implemented in the photo-detector 2 in order to measure a light reflectance with respect to light of each wavelength, the spectral means may be provided in the side of the light source. If a reflectance of light of a single wavelength or merely entire light is measured, the photo-detector is not needed and only one sensor element is needed. Moreover, the present invention may be adapted to not only en spectroscopic reflectometer but also light reflectance measuring device.

Further, the present invention is not limited to the embodiments mentioned above, and various changes within the scope are possible without departing from the spirit of the invention.

REFERENCE SIGNS LIST

100 . . . spectroscopic reflectometer
4 . . . head
2 . . . photo-detector
5 . . . reflectance calculation unit
8 . . . internal reflection mechanism
3 . . . beam splitter
$SP_b$ . . . dark sample
$SP_r$ . . . calibration sample
$SP_s$ . . . inspection work

The invention claimed is:
1. A spectroscopic reflectometer for use with a sample, the spectroscopic reflectometer comprising:
a head comprising:
a light source;
a photo-detector; and
an internal reflection mechanism; and
a reflectance calculation unit;

wherein the light source is structured to project a measurement light the sample and introduce reflection light from the sample irradiated by the measurement light;
the photo-detector is structured to detect an intensity of the reflection light, having its light receiving part placed in a position at which the reflection light introduced into the head arrives;
the internal reflection mechanism has a constant light reflectance and is placed in a position at which a part of the measurement light arrives, and is structured such that the reflection light reflected by the internal reflection mechanism reaches the light receiving part of the photo-detector within the head;
the reflectance calculation unit comprises a memory structured to store a first output value from the photo-detector, a second output value from the photo-detector, a third output value from the photo-detector, a fourth output value from the photo-detector, a fifth output value from the photo detector; and a sixth output value from the photo-detector;
the first output value is an output value of the photo-detector in a state of substantially no light being introduced;
the second output value that is an output value of the photo-detector when the sample is a dark sample that substantially reflects no light;
the third output value is an output value of the photo-detector when a calibration sample of a known light reflectance is used as the sample;
the fourth output value is an output value of the photo-detector in a state of substantially no light being introduced;
the fifth output value is an output value of the photo-detector when the dark sample is used as the sample; and
the sixth output value is an output value of the photo-detector when an inspection work to be measured is used as the sample;
the photo-detector and the reflectance calculation unit are structured to measure and store the first output value, the second output value, and the third output value during a subordinate period in which variation in the output value of the photo-detector is substantially negligible;
the photo-detector and the reflectance calculation unit are structured to measure and store the fourth output value, the fifth output value, and the sixth output value during a main measurement period in which variation in the output value of the photo-detector is substantially negligible; and
the reflectance calculation unit comprises a processor structured to calculate light reflectance of the inspection work based on the first output value, the second output value, the third output value, the fourth output value, the fifth output value, and the sixth output value stored in the memory.

2. The spectroscopic reflectometer according to claim 1, further comprising a beam splitter which is arranged inside a main body of the head so that a part of the measurement light is reflected by the beam splitter to irradiate the object and a part of the measurement light is passed through the beam splitter to irradiate the internal reflection mechanism, and in the meanwhile, the reflection light reflected by the object is passed through the beam splitter to be guided to the photo-detector, and the reflection light reflected by the internal reflection mechanism is reflected to be guided to the photo-detector.

3. The spectroscopic reflectometer according to claim 1, wherein the dark sample is incidental to the head movably and detachably between an irradiation position which is irradiated by the measurement light and an evacuation position which is not irradiated by the measurement light.

4. The spectroscopic reflectometer according to claim 1, wherein the reflectance calculation unit is structured to calculate the light reflectance of the inspection work based on the following equation:

$$R_s = \frac{(I'_s - I'_b)(I_b - I_d)}{(I'_b - I'_d)(I_r - I_b)} R_r$$

wherein $I_d$ is the first output value, $I_b$ is the second output value, $I_r$ is the third output value, $I_d'$ is the fourth output value, $I_b'$ is the fifth output value, $I_s'$ is the sixth output value, $R_r$ is a reflectance of the calibration sample, and $R_s$ is the light reflectance of the inspection work.

5. A non-transitory computer-readable medium storing computer-executable instructions that, when executed by a computer connected to a spectroscopic reflectometer comprising a light source, a photo-detector, and an internal reflection mechanism, wherein the source projects measurement light to a sample and introduces reflection light, the photo-detector detects an intensity of the reflection light, and the internal reflection mechanism is placed in a position at which a part of the measurement light arrives and is structured such that the reflection light reflected by the internal reflection mechanism reaches the light receiving part of the photo-detector, cause the computer to perform:

measuring and storing a first output value, a second output value, and a third output value during a subordinate period in which variation of the output of the photo-detector is substantially negligible, wherein the first output value is an output value of the photo-detector in a state of substantially no light being introduced, the second output value is an output value of the photo-detector when the sample is a dark sample that substantially reflects no light, and the third output value is an output value of the photo-detector when a calibration sample of a known light reflectance is used as the sample;

measuring and storing a fourth output value, a fifth output value, and a sixth output value during a main measurement period in which variation in the output value of the photo-detector is substantially negligible, wherein the fourth output value is an output value of the photo-detector in a state of substantially no light being introduced; the fifth output value is an output value of the photo-detector when the dark sample is used as the sample; and the sixth output value is an output value of the photo-detector when an inspection work to be measured is used as the sample; and, calculating reflectance of the inspection work based on the first output value, the second output value, the third output value, the fourth output value, the fifth output value, and the sixth output value.

6. The computer-readable medium according to claim 5, wherein the light reflectance of the inspection work is calculated based on the following equation:

$$R_s = \frac{(I'_s - I'_b)(I_b - I_d)}{(I'_b - I'_d)(I_r - I_b)} R_r$$

wherein $I_d$ is the first output value, $I_b$ is the second output value, $I_r$ is the third output value, $I_d'$ is the fourth output value, $I_b'$ is the fifth output value, $I_s'$ is the sixth output value, $R_r$ is a reflectance of the calibration sample, and $R_s$ is the light reflectance of the inspection work.

* * * * *